United States Patent [19]
Goldenberg

[11] Patent Number: 5,665,094
[45] Date of Patent: Sep. 9, 1997

[54] APPARATUS FOR ASPIRATING AND COLLECTING MIDDLE EAR SPECIMENS

[76] Inventor: Robert Arlin Goldenberg, 501 Stonehaven Rd., Dayton, Ohio 45429

[21] Appl. No.: 556,046

[22] Filed: Nov. 13, 1995

[51] Int. Cl.$^6$ ............................................. A61F 11/00
[52] U.S. Cl. .......................... 606/109; 128/765; 604/212
[58] Field of Search ............................ 606/109, 108, 606/172, 1; 604/131, 132, 133, 181, 187, 190; 128/212, 765

[56] References Cited

U.S. PATENT DOCUMENTS

| | | |
|---|---|---|
| 69,110 | 9/1867 | Mattson . |
| 2,176,366 | 10/1939 | Smith . |
| 2,642,064 | 4/1953 | Lawshe ........................... 604/212 |
| 2,722,257 | 2/1955 | Lockhart ......................... 604/212 |
| 3,089,489 | 5/1963 | Dumire . |
| 3,450,129 | 6/1969 | Avery et al. . |
| 3,590,722 | 7/1971 | Leptrone ........................... 604/212 |
| 3,645,268 | 2/1972 | Capote . |
| 3,989,045 | 11/1976 | Van Eck ........................... 604/212 |
| 4,108,175 | 8/1978 | Orton . |
| 4,334,538 | 6/1982 | Juhn . |
| 4,411,265 | 10/1983 | Eichenlaub . |
| 4,641,663 | 2/1987 | Juhn . |
| 4,760,847 | 8/1988 | Vaillancourt . |
| 4,766,908 | 8/1988 | Clement . |
| 5,254,120 | 10/1993 | Cinberg et al. . |
| 5,476,446 | 12/1995 | Arenburg ........................... 604/21 |

*Primary Examiner*—Robert A. Hafer
*Assistant Examiner*—Justine R. Yu
*Attorney, Agent, or Firm*—Killworth, Gottman, Hagan & Schaeff, LLP

[57] ABSTRACT

The present invention is an apparatus and method for aspirating and collecting a middle ear fluid specimen through the ear drum of a patient. Broadly, the present invention involves using a hollow needle that is adapted for puncturing through the ear drum. The hollow needle is mountable on a bulb, and the bulb is operatively adapted to draw a specimen of middle ear fluid into the hollow needle when the needle is mounted on the bulb. Such an apparatus can be made inexpensively and disposable after each use. Mounting the hollow needle on the bulb makes the present invention self-contained by eliminating the need for an external vacuum source. One possible feature of the present invention is a stop guard that is secured to the outside of the hollow needle. The stop guard is adapted to inhibit penetration of the hollow beyond a desired depth through an ear drum. That is, once the desired depth through the ear drum is reached, the stop guard provides enough resistance to further penetration that a practitioner can tell that the desired depth has been reached. Thus, with this feature, the depth of penetration through the ear drum can be determined without having to rely solely on the skill of the practitioner performing the procedure.

20 Claims, 2 Drawing Sheets

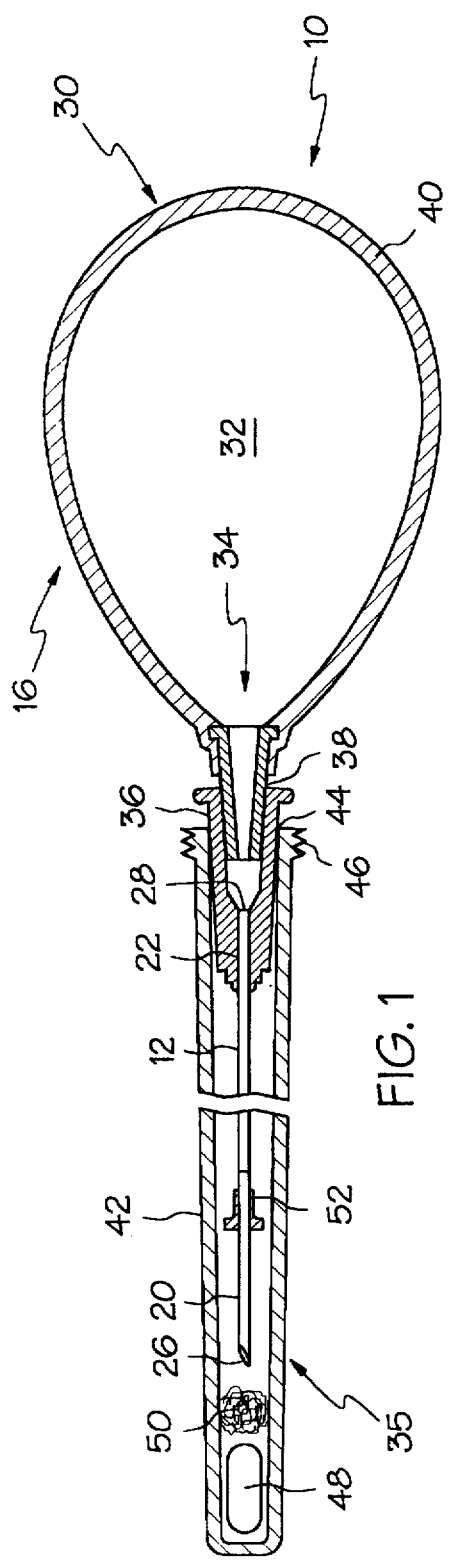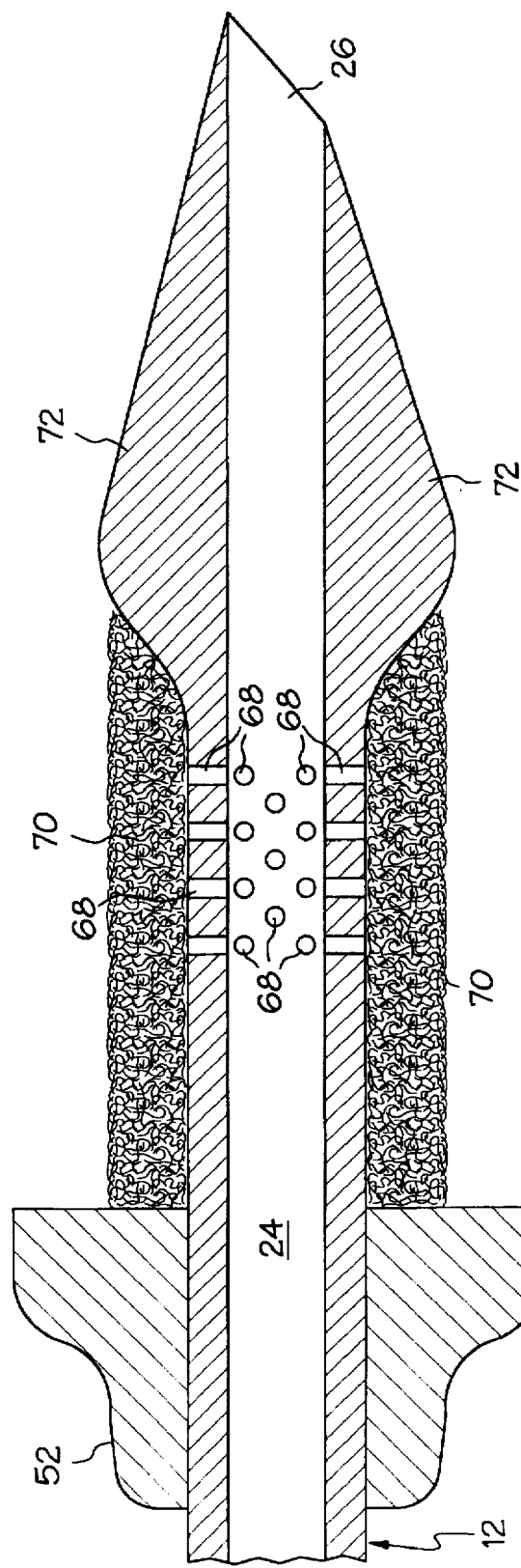

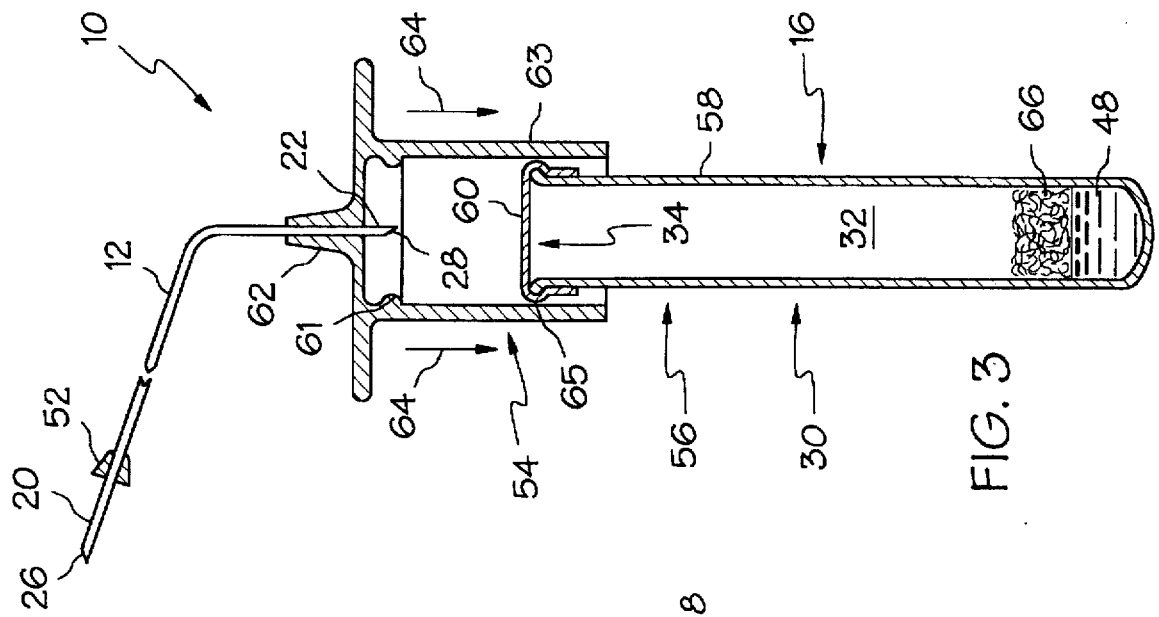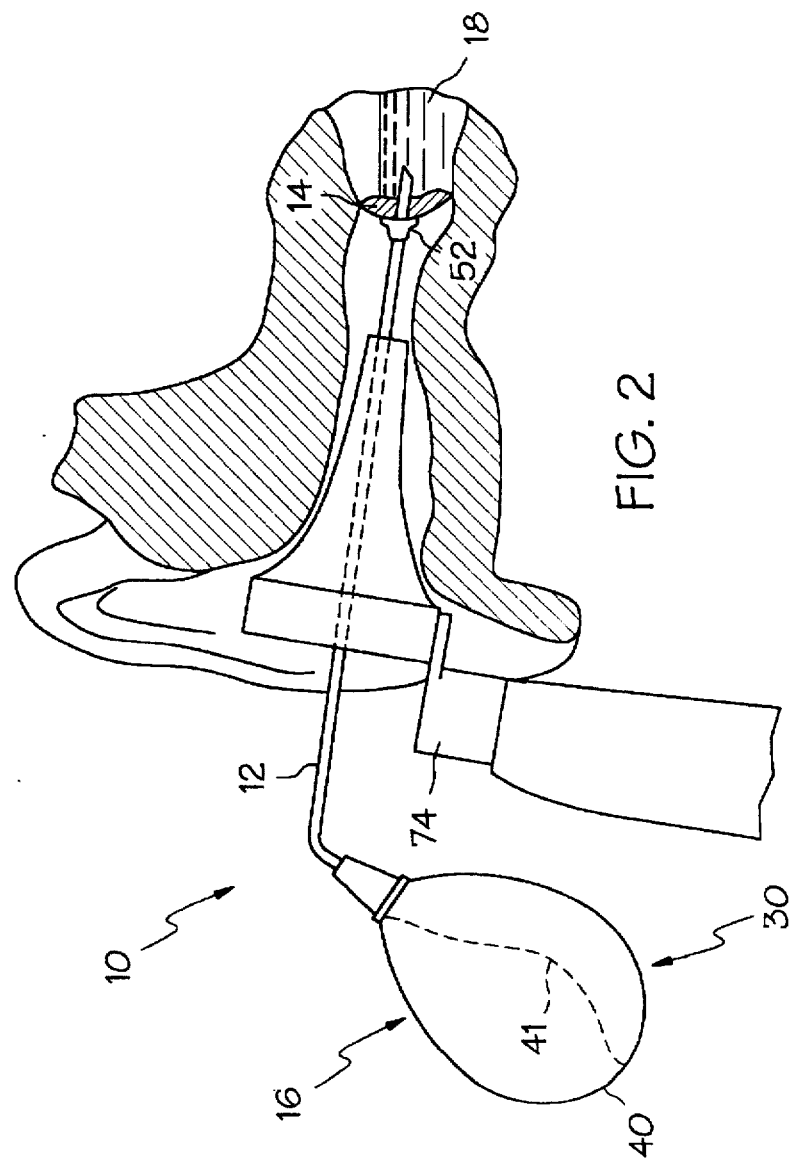

APPARATUS FOR ASPIRATING AND COLLECTING MIDDLE EAR SPECIMENS

FIELD OF THE INVENTION

The present invention is related to techniques for removing fluid specimens (e.g., pus and other secretions) from the middle ear space of a patient, and more particularly to an apparatus for aspirating and collecting middle ear specimens through the ear drum without using an external suction pump.

BACKGROUND OF THE INVENTION

Recent medical studies have found that antibiotic resistant bacterial organisms are becoming more and more prevalent. Most bacterial infections are cultured and the type of bacteria causing the infection identified before an antibiotic treatment is prescribed. Infections of the middle ear (i.e., otitis media) are one of the few bacterial infections which are routinely treated without first being cultured and the bacterial strain identified. In general, without a pre-treatment identification of each bacterial strain present in the infected area, there is a risk that the chosen antibiotic treatment will be ineffectual. This risk has increased with the ever increasing number of antibiotic resistant bacteria. Depending on the type of infection, prescribing an ineffectual treatment can unnecessarily prolong a patient's pain and suffering and may even result in further complications from recurrent otitis media.

One main reason bacterial ear infections are typically not cultured and identified before being treated is because the ability to aspirate a specimen from the middle ear space has been limited by the equipment and devices previously used for that purpose. One such prior aspirator had a handle at one end which was connected to a vacuum pump, a hollow needle at its other end and a vial attached to the handle for collecting aspirated fluid. The needle was inserted through a patient's ear drum (i.e., tympanic membrane) and the vacuum pump was operated to establish a vacuum used to withdraw fluid from the middle ear space and collect the fluid in the vial. One problem with this type of collection system is the need for an external vacuum pump. Such mechanical vacuum pumps are expensive and not always available when and where needed, for example, in many less developed countries and underserved areas of even major industrialized countries. Because some type of tubing and connector is needed to connect the aspirator to the external vacuum pump, this type of collection system can be cumbersome and unwieldy, making it difficult to collect a specimen of middle ear fluid.

An aspirator which does not require an external vacuum source is disclosed in U.S. Pat. No. 4,641,663. This aspirator is a hypodermic needle assembly with a plunger which is spring loaded to draw fluid through its hollow needle once a latch mechanism is released. While this type of aspirator is self-contained (i.e., does not use an external suction pump or vacuum source) and disposable, this aspirator is still relatively complex and, thus, expensive to manufacture. A problem shared by both of the above described prior aspirators is that the depth of penetration by the hollow needle, into the middle ear space, is largely dependent on the skill and experience of the person performing the procedure. Thus, the use of either of these aspirators is likely to be limited to only the most experienced practitioners.

Therefore, especially with the apparent continued proliferation of antibiotic resistant bacteria, there is an increasing need for a disposable and inexpensive apparatus for aspirating and collecting a fluid specimen from the middle ear space of a patient without the need of an external vacuum source (i.e., self-contained). There is a further need for such an apparatus which does not rely solely on the practitioner's skill to determine the depth of penetration through the ear drum.

SUMMARY OF THE INVENTION

These needs are met by providing an apparatus and method, according to the principles of the present invention, for aspirating and collecting a middle ear fluid specimen through the ear drum of a patient. Broadly, the present invention involves using a hollow needle that is adapted for puncturing the ear drum. The hollow needle is mountable on a bulb, and the bulb is operatively adapted to draw a specimen of middle ear fluid into the hollow needle when the needle is mounted on the bulb. Such an apparatus can be made inexpensively and disposable after each use. Mounting the hollow needle on the bulb makes the present invention self-contained by eliminating the need for an external vacuum source.

In one aspect of the present invention, an apparatus is provided which comprises a hollow needle having a distal end adapted for puncturing through the ear drum of a patient, a proximal end and a bore connecting a first hole at the distal end with a second hole at the proximal end. The apparatus further comprises a bulb having a wall which at least partially defines a chamber and an opening leading into the chamber. The proximal end of the hollow needle is permanently or removably mountable to the bulb so as to bring the second hole in fluid communication with the chamber through the opening. The hollow needle can either be directly mounted to the bulb, or a hub can be used to mount the proximal end of the hollow needle to the bulb. The hub, itself, can then be permanently or removably mounted to the bulb so that the second hole at the proximal end is in fluid communication with the chamber of the bulb through the hub and the opening. The hollow needle can be permanently mounted to the bulb, for example, by bonding the proximal end of the needle in the opening, molding the needle in place during the forming of the bulb or by any other suitable means. The hollow needle can be removably mounted to the bulb, for example, by using a threaded connection, an interference or press fit connection, a luer-lock connection, or any other suitable connecting system. The bulb is operatively adapted to draw a specimen of middle ear fluid through the first hole at the distal end of the hollow needle at least part way into the bore of the hollow needle, and possibly into the bulb itself, depending on the amount and viscosity of the fluid.

One type of bulb which can be used with the present apparatus includes a wall that is collapsible and self- or otherwise recoverable from a collapsed state. The wall is resilient enough to sufficiently recover, from a collapsed condition, to draw a specimen of middle ear fluid through the first hole and into the bore of the hollow needle. Alternatively, the bulb can also be a self contained vacuum bulb, where the chamber is at least partially evacuated and capable of being placed in fluid communication with the bore of the hollow needle through the second hole at the proximal end. There is a sufficient vacuum in the evacuated chamber to draw a specimen of middle ear fluid through the first hole at the distal end and into the bore of the hollow needle. One example of a self contained vacuum bulb includes a tube having a membrane covered opening leading into the evacuated chamber. With such a self contained vacuum bulb, the proximal end of the hollow needle is adapted for puncturing the membrane in order to place the evacuated chamber in fluid communication with the bore of the hollow needle. This type of self contained vacuum bulb has been used to draw blood from a patient's vein.

The bulb can be operatively adapted to draw a specimen of middle ear fluid through the hollow needle and into the chamber of the bulb. With such an embodiment, it is desirable to close the opening after the hollow needle is removed. The opening can be adapted to include any suitable structure which enables the opening to be closed to prevent the specimen from being contaminated. For example, the hollow needle can be removed and the opening of the bulb closed with a cap or a plug. When the middle ear specimen is retained in the bulb, the opening of the bulb can also be effectively closed by leaving the hollow needle in place on the bulb and covering the needle with a protective sheath. In addition, it may be desirable for a preservative to be kept in the chamber of the bulb for preserving the middle ear specimen, drawn into the chamber, for subsequent culturing and identification.

As an alterative to using the bulb to store the fluid specimen, a separate specimen container with an opening can be used. Such a container is adapted to allow the distal end of the hollow needle through its opening. It may also be desirable for a preservative, suitable for preserving the middle ear specimen for subsequent culturing and identification, to be disposed within the separate specimen container.

One possible feature of the present invention is a stop guard that is secured to the outside of the hollow needle. The stop guard is adapted to inhibit penetration of the hollow needle beyond a desired depth through an ear drum. That is, once the desired depth through the ear drum is reached, the stop guard provides enough resistance to further penetration that a practitioner can tell that the desired depth has been reached. Thus, with this feature, the depth of penetration through the ear drum can be determined without having to rely solely on the skill of the practitioner performing the procedure.

A middle ear specimen can also be collected for culturing and identification, according the present invention, by forming one or more perforations through the tubular wall of the hollow needle and disposing a fluid absorbent material on the outside of the needle and adjacent to the one or more perforations. In this way, when a fluid specimen is drawn up into the hollow needle at the point where the one or more perforations are located, the absorbent material is in position to absorb at least part of the fluid specimen. If need be, the fluid can be drawn up into the hollow needle a number of times until enough of the fluid is absorbed by the absorbing material to constitute a satisfactory specimen for culturing.

When a stop guard is secured to the hollow needle, as described above, it may be desirable for the one or more perforations to be disposed between the stop guard and either the first hole at the distal end or the second hole at the proximal end of the hollow needle. With the one or more perforations and the absorbing material positioned between the stop guard and the distal end of the hollow needle, the absorbent material is in position to directly absorb middle ear fluid, by direct contact while being immersed in the fluid, as well as through the perforations, as described above. With the one or more perforations and the absorbing material positioned between the stop guard and the proximal end of the hollow needle, middle ear fluid can be drawn up into the hollow needle a number of times by keeping the needle inserted through the ear drum and collapsing the bulb slow enough to allow the air to gradually escape out through the at least one perforation and then by allowing the bulb to recover quickly enough to draw fluid up into the hollow needle even while some air may be sucked in through the at least one perforation.

In one possible modification to this embodiment, when the absorbing material is disposed so as to pass through the ear drum, the distal end of the hollow needle can be flared to protect the absorbing material (i.e., flared so as to be generally flush with or extend radially out beyond the outer surface of the absorbent material). In this way, portions of the absorbing material can be prevented from being dislodged while the distal end of the needle is forced through and removed from the ear drum. It may also be desirable to dispose the absorbent material onto the distal end of the hollow needle, even if there are no perforations. If a sufficient amount of middle ear fluid cannot be drawn into the hollow needle, an additional amount of the fluid can be obtained from the absorbent material.

It may be desirable for a medicine to be disposed in the bore of the hollow needle. For example, the bore of the hollow needle can contain an anesthetic for deadening the pain at the puncture site in the ear drum. In addition, the bore of the hollow needle can contain an antibiotic for fighting the infection. When the bulb is collapsible and self- or otherwise recoverable from a collapsed state and the hollow needle is mounted thereon, air can be forced out through the distal end of the hollow needle, by collapsing the bulb, to expel the medicine.

In another aspect of the present invention, a method is provided comprising the steps of: providing a hollow needle mountable on a bulb; inserting the hollow needle through the ear drum of a patient; causing the bulb to draw a specimen of middle ear fluid into the hollow needle; and withdrawing the hollow needle from the ear of the patient. The hollow needle being provided is adapted for puncturing through the ear drum of a patient, and the bulb is operatively adapted to draw a specimen of middle ear fluid into the hollow needle when the needle is mounted on the bulb.

When the hollow needle is mounted on the bulb and the bulb is collapsible and self- or otherwise recoverable from a collapsed state, the step of causing the bulb to draw a specimen includes collapsing the bulb so as to force air out through the hollow needle before or after the needle is inserted through the ear drum and then allowing the collapsed bulb to recover enough to draw a specimen of middle ear fluid into the hollow needle.

It may be desirable for the aspirated middle ear specimen to be kept in a separate specimen collection container. When a separate specimen container and a collapsible-type bulb is used, the preceding method includes causing the bulb to at least partially collapse, after the hollow needle is withdrawn from the ear, to thereby force the specimen of middle ear fluid out of the hollow needle and into the specimen collection container. The specimen collection container can be any structure suitable for keeping the aspirated specimen in condition for subsequent culturing and identification. (e.g., a test tube, a sheath suitable for receiving and being secured to the hollow needle, etc.). It may be desirable for the specimen collection container to include a preservative (i.e., any suitable medium for keeping bacteria in the specimen viable for subsequent culturing and identification).

The bulb being provided for use in the present method can also be a self contained vacuum bulb having an evacuated chamber therein. With such a bulb, the bore of the hollow needle is brought into communication with the evacuated chamber in order to draw a specimen of middle ear fluid into the hollow needle.

Rather than directing the specimen of middle ear fluid into a separate specimen collection container, the bulb can be caused to further draw the specimen into a chamber within the bulb. For example, if the bulb is the collapsible type, the bulb can be collapsed enough to produce a sufficient suction force to draw the fluid specimen through the hollow needle and into the bulb chamber. If the bulb is a self contained vacuum bulb, its chamber can be sufficiently evacuated to draw the fluid specimen into the chamber. In this way, the bulb itself functions as the specimen collection container. As with the separate container, a preservative can also be disposed inside the bulb and the specimen brought into contact with the preservative.

When the hollow needle is inserted through the ear drum, a stop guard can be secured to the hollow needle and adapted to at least inhibit, if not prevent, full penetration of the hollow needle through the ear drum.

When the tubular wall of the hollow needle is provided with one or more perforations and a fluid absorbent material is disposed on the outside of the hollow needle so as to absorb fluid present in the one or more perforations, the step of causing the bulb to draw a specimen into the hollow needle includes drawing the specimen to at least one perforation so that at least a portion of the specimen is absorbed into the absorbent material.

The objectives, features, and advantages of the present invention are apparent upon consideration of the present specification and the appended drawings.

BRIEF DESCRIPTION OF THE DRAWINGS

FIG. 1 is a sectional side view of one embodiment of the present apparatus for aspirating and collecting a middle ear fluid specimen through the ear drum of a patient, with a collapsible bulb;

FIG. 2 is a side view of another embodiment of the present apparatus in position to aspirate and collect a fluid specimen, with the ear of a patient shown in cross-section;

FIG. 3 is a sectional side view of an additional embodiment of the present apparatus, with a self contained vacuum bulb; and FIG. 4 is an enlarged sectional view of one embodiment of a distal end of the hollow needle used to form part of an apparatus of the present invention.

DETAILED DESCRIPTION OF THE INVENTION

Although the present invention is herein described in terms of specific embodiments, it will be readily apparent to those skilled in this art that various modifications, re-arrangements, and substitutions can be made without departing from the spirit of the invention. The scope of the present invention is thus only limited by the claims appended hereto.

An apparatus 10, according to the present invention, broadly includes a hollow needle 12, such as a conventional hypodermic needle or any other needle adapted for puncturing through the ear drum 14 of a patient (see FIG. 2). The hollow needle 12 is mountable on a bulb 16. The bulb 16 is operatively adapted to draw a specimen of middle ear fluid 18 (see FIG. 2) into the hollow needle 12 when the needle 12 is so mounted. The needle 12 can be straight or formed with a desired bend and is sufficiently long to reach and penetrate the ear drum 14. The hollow needle 12 has a pointed distal end 20, for puncturing through the ear drum 14, a proximal end 22 and a bore 24. The bore 24 connects a first hole 26 at the distal end 20 with a second hole 28 at the proximal end 22. The bulb 16 of each apparatus 10 has a wall 30 which at least partially defines a chamber 32 and a first opening 34 which leads into the chamber 32. The proximal end 22 of the hollow needle 12 is permanently or removably mountable to the bulb 16 so as to bring the second hole 28 in fluid communication with the chamber 32 through the first opening 34.

Referring to FIG. 1, one embodiment of apparatus 10, generally designated by the reference numeral 35, comprises a hollow needle 12 that is straight and includes a hub 36 like that found on a convention hypodermic needle. The hub 36 is used to mount the proximal end 22 of the hollow needle 12 to the bulb 16. The hub 36 can be removably mounted to the bulb 16, for example, by using an interference or press fit connection between a tapered hollow tip 38, mounted in the opening 34 of the bulb 16, and the hub 36. Rather than using an interference or press fit, a threaded connection, a luer-lock connection or any other suitable connecting system can be used to removably connect together the hub 36 and the hollow tip 38. The hollow needle 12 can also be permanently mounted to the bulb 16, for example, by bonding the wall 30 of the bulb 16 directly around the hub 36, instead of using the intermediate hollow tip 38. Alternatively, the hollow needle 12 can be directly mounted to the bulb 16, for example, by molding or otherwise bonding the wall 30 of the bulb 16 directly around the needle 12. With the hollow needle 12 permanently or removably mounted to the bulb 16, the bulb 16 is operatively adapted to draw a specimen of middle ear fluid 18 through the first hole 26 at the distal end 20 at least part way into the bore 24 of the hollow needle 12.

One type of bulb 16 which can be used with the apparatus 35, as shown in FIGS. 1 and 2 and designated by the reference numeral 40, includes a wall 30 that is collapsible and self- or otherwise recoverable from a collapsed stated. The collapsed state of bulb 40 is shown in FIG. 2 and designated by the phantom line 41. With a collapsible-type bulb 40, the wall 30 is able to self- or otherwise recover enough from a collapsed condition, to draw a specimen of middle ear fluid 18 through the first hole 26 and into the bore 24 of the hollow needle 12. The wall 30 of the collapsible bulb 40 can be made from any sufficiently resilient material, such as a rubber or other resilient polymeric materials. It is desirable for the wall 30 of any bulb 16 to be transparent.

A separate specimen container 42 can be used to store a specimen of the middle ear fluid 18. The specimen container 42, for example, can be in the form of a sheath, similar to those used to protect conventional hypodermic needles. The sheath 42 has a second opening 44 through which the needle 12 is disposed when the specimen of fluid 18 is transferred to the container 42. The sheath 42 can be adapted to receive the full length of the needle 12 and so that the hub 36 seats inside its opening 44, such as with an interference or press fit, as shown. It is desirable to close the second opening 44 of the specimen container 42 to prevent the specimen from being inadvertently lost or contaminated. The second opening 44 can be closed by removing the hollow needle 12 and closing the opening 44 with a cap or plug (not shown) disposed around the outside or inside the opening 44, respectively. For example, the outer portion of the container 42 forming its opening 44 can be formed into threads 46 adapted for receiving mating threads on the inside of a cap. Alternatively, a plug (not shown) similar to hub 36 can be interference or press fit inside the opening 44 to close the container 42. It is also possible to effectively close the container 42 by leaving the hub 36 in place in the opening 44 of container 42 and the tip 38, with the bulb 16, in place in the hub 36. In this way, a sterile non-contaminated environment can be maintained around the culture specimen.

Alternatively, rather than using a separate specimen container 42, it may be desirable to operatively adapt the bulb 40 to draw a specimen of the middle ear fluid 18 through the hollow needle 12 and into the chamber 32 so as to be stored in the bulb 40, itself. Once the specimen is inside the bulb 40, the first opening 34 leading into the chamber 32 can be adapted to include any suitable structure which enables the opening 34 to be closed to prevent the specimen from being inadvertently lost or contaminated. For example, the hub 36 can be removed from the tip 38 and the opening 34 of the bulb 40 closed which a cap (not shown) adapted to form an interference or press fit on the outside of the tip 38, in a manner similar to that of hub 36. Instead of a cap, a plug (not shown) could be used to seal the chamber 32 closed, by forming an interference or press fit inside the opening 34 of the tip 38. The first opening 34 of the bulb 40 can also be effectively closed by leaving the hub 36 of the hollow needle 12 in place on the hollow tip 38 and covering the needle 12 with the protective sheath 42, as described above.

Regardless of where the specimen of middle ear fluid 18 is kept, it may be desirable to use a preservative 48 which is suitable for preserving the specimen of middle ear fluid 18 in condition for subsequent culturing and identification. The preservative 48 may be, for example, a liquid such as distilled water, saline solution, or other non-reactive liquid which will provide an environment in which the bacteria will remain viable for subsequent culturing. The preservative 48 may also be one or a combination of Stuart's Medium, Bartel's Biotransport Medium and thioglycollate. Regardless of whether the specimen of middle ear fluid 18 is stored in the separate specimen container 42 or the collapsible-type bulb 40, it may be desirable for the preservative 48 to be free to move about. It may also be desirable for the preservative 48 to be kept constrained within a frangible ampoule, like that disclosed in U.S. Pat. No. 3,450,129, which is incorporated herein by reference in its entirety. The preservative 48 can be sealed within any other suitable type of frangible packaging structure disposed inside either the chamber 32 of bulb 40 or the specimen container 42. An optional plug 50 made of an absorbent material, such as cotton swab material, can be snugly disposed (i.e., in a tight fit) within the sheath 42 to prevent the ampoule from sliding toward the second opening 44 and retain the loose ampoule of preservative 48 adjacent to the closed end of the sheath 42. When the preservative 48 is kept in a frangible ampoule, it is desirable for the wall of the container 42 to be collapsible in order to fracture the ampoule and release the liquid preservative 48. If desirable, the plug 50 may also be adapted to prevent the released liquid preservative 48 from flowing toward the second opening 44 of the sheath 42.

It is desirable for a stop guard 52 to be mounted or otherwise disposed on the hollow needle 12 to inhibit penetration of the needle 12 beyond a desired depth through the ear drum 14 (see FIG. 2). That is, once the desired depth through the ear drum 14 is reached, the stop guard 52 provides enough resistance to further penetration that a practitioner handling the apparatus 10 can tell that the desired depth has been reached. Thus, the depth of penetration through the ear drum 14 can be determined without having to rely solely on the skill of the practitioner performing the procedure.

It is believed that a number of suitable designs for the stop guard 52 are feasible. For example, the stop guard 52 can be a ring formed around the outside of the hollow needle 12. The ring shaped stop guard 52 can be bell shaped (see FIGS. 1, 2 and 4), cone-shaped (see FIG. 3) or any other suitable configuration. It is desirable for the stop guard 52 to be bonded or otherwise fixed at a desired location on the hollow needle 12. To this end, the stop guard 52 can be manufactured as an integral part of the needle 12, such as when the needle 12 is molded using a plastic material. Alternatively, it may be desirable to make the location of the stop guard 52, on the needle 12, adjustable. This adjustability can be obtained by making the stop guard 52 with an inside diameter that forms an interference or press fit when slipped over the needle 12. Such a stop guard 52 can be made adjustable and still sufficiently inhibit further penetration of the needle 12 through the ear drum 14 by adjusting the strength of the interference or press fit (i.e., varying the inside diameter of and/or the material used to make the stop guard 52).

Referring to FIG. 3, in an alternative embodiment of the apparatus 10, generally designated by the reference numeral 54, the bulb 16 is a self contained vacuum bulb 56 with its chamber 32 being at least partially evacuated and capable of being placed in fluid communication with the bore 24 of the hollow needle 12 through the second hole 28 at the proximal end 22. The chamber 32 of the self contained vacuum bulb 56 is sufficiently evacuated to draw a specimen of middle ear fluid 18 through the first hole 26 and into the bore 24 of the needle 12, when the needle 12 and evacuated chamber 32 are placed in fluid communication. The self contained vacuum bulb 56 comprises, for example, a rigid walled test tube 58 with its opening 34 covered by a membrane 60. Alternatively, instead of being test tube shaped, the self contained vacuum bulb 56 can be balloon shaped, similar to the bulb 40 of FIGS. 1 and 2. With such a self contained vacuum bulb 56, the proximal end 22 of the hollow needle 12 is adapted for puncturing the membrane 60 in order to place the evacuated chamber in fluid communication with bore 24 of the needle 12. For example, like the distal end 20, the proximal end 22 of the needle 12, can be pointed. It is desirable for the membrane 60 to be made out of a material which will maintain an adequate seal between the needle 12 and the punctured membrane 60. It is believed that a resilient material, such as an elastomeric polymer, will suffice.

It is desirable to secure the needle 12 of apparatus 54 in place while the needle 12 is in fluid communication with the evacuated chamber 32 of the self contained vacuum bulb 56. This can be accomplished by mounting the needle 12 in a cap 62 adapted so as to be secured in place over the opening 34 of the self contained vacuum bulb 56. For example, the cap 62 can include an annular protuberance 61, located inside the cap 62 and adapted for being snapped in place over the outer circuferential edge or lip 65 of the opening 34 by moving the cap 62 in the direction indicated by the arrows 64. The cap 62 and the self contained vacuum bulb 56 can also be adapted to function like a syringe. For example, as shown, the cap 62 can include a tubular section 63 which functions as the barrel of the syringe. The self contained vacuum bulb 56 can be adapted to function like the plunger of a syringe, with the portion of the membrane 60 on the outer circumferential edge 65 sealing against the inside surface of the tubular section 63.

The pointed proximal end 22 of the needle 12 should extend a sufficient distance down from the cap 62 to insure that the membrane 60 will be punctured by the end 22 when the cap 62 is secured in place, for example, when the circumferential edge 65 is snapped in place past the annular protuberance 61 or simply when the membrane 60 seals against the inner surface of the tubular section 63. It is desirable for the membrane 60 to be made out of a material which will maintain an adequate seal between the tubular section 63 and the membrane 60 and/or between the needle 12 and the punctured membrane 60 (as discussed above). It is believed that a resilient material, such as a rubber or other elastomeric polymer, will suffice. At the same time, it is desirable for the pointed proximal end 22 of the needle 12 to only extend down from the cap 62 enough to puncture the membrane 60 as the cap 62 is about to be secured in place over the opening 34 of the self contained vacuum bulb 56.

It may be desirable for the evacuated chamber 32 of the self contained vacuum bulb 56 to contain a preservative 48. However, because the self contained vacuum bulb 56 is rigid walled, the preservative 48 is not in a frangible ampoule or otherwise separately packaged. Therefore, it may be desirable to dispose a plug 66 of a fluid absorbent material, such as cotton swab material, snugly within the tube 58 and above the preservative 48. In some cases, it may also be desirable for the preservative 48 to be loose and free to move around within the chamber 32.

Referring to FIG. 4, it may be desirable to modify the distal end 20 of the hollow needle 12 by forming one or more perforations 68 through the tubular wall of the hollow needle 12 and securing, for example, a ring-shaped mat 70 of a fluid absorbent material, on the outside of the perforated portion of the needle 12. This fluid absorbant material may include, for example, one or a combination of cotton, cotton-wool, Dacron® and calcium alginate, to name a few. The mat 70 can be made, for example, from cotton swab material or cotton fiber wrapped around the needle 12. In this way, when a specimen of middle ear fluid 18 is drawn up into the hollow needle 12 at the point where the perforations 68 are located, the absorbent mat 70 is in position to absorb at least part of the fluid 18. In addition, if necessary, the fluid 18 can be drawn up into the hollow needle 12 a number of time until enough of the fluid 18 is absorbed by the mat 70 to constitute a satisfactory specimen for subsequent culturing and identification.

When a stop guard 52 is secured to the hollow needle 12, as described above, it may be desirable for the perforations 68 to be disposed between the stop guard 52 and the first hole 26 at the distal end 20 (as shown in FIG. 4) or between the stop guard 52 and the proximal end 22 of the hollow needle 12. With the perforations 68 and the mat 70 of absorbing material positioned between the stop guard 52 and the distal end 20, the ring-shaped mat is in position to absorb middle ear fluid 18, by direct contact while being immersed in the fluid 18, as well as through the perforations 68, as described above. Regardless of whether a stop guard 52 is used or not, it is desirable for the distal end 20 of the needle 12 to have a flared portion 72 behind which the mat 70 is disposed and protected, to help prevent portions of the mat 70 from being dislodged while the distal end 20 of the needle 12 is forced through and removed from the ear drum 14. It may also be desirable to dispose the mat 70 of absorbent material on the distal end 20 of the hollow needle 12, even if no perforations 68 are used. If a sufficient amount of middle ear fluid 18 cannot be drawn into the hollow needle 12, an additional amount of the fluid 18 can be obtained from the absorbent material of mat 70.

If the perforations 68 and the mat 70 of absorbing material are positioned between the stop guard 52 and the proximal end 22 of the hollow needle 12, it may be necessary to draw the middle ear fluid 18 up into the hollow needle 12 a number of times in order for the mat 70 to absorb a sufficient amount of fluid 18. This may be accomplished by keeping the needle 12 inserted through the ear drum 14, collapsing the bulb 40 so as to allow air to gradually escape out through the perforations 68 and then allowing the bulb 16 to recover quickly enough to draw fluid up into the hollow needle 12 even while some air may be sucked in through the perforations 68.

During the collection of a specimen of middle ear fluid 18 according to the present invention, it is desirable to use a conventional otoscope 74 having a speculum 76 with any of the embodiments of apparatus 10 (see FIG. 2). In one method for aspirating and collecting a specimen of middle ear fluid 18, the otoscope 74 is inserted into the patient's ear and used to locate the ear drum 14. The hollow needle 12 is then inserted through the speculum 76 of the otoscope 74 and the distal end 20 is forced through the ear drum 14 until the stop guard 52 makes contact with the ear drum 14. When a collapsible bulb 40 is used, its wall 30 is collapsed (indicated by phantom line 41) before the distal end 20 of needle 12 is forced through the ear drum 14. With the bulb 40 in its collapsed state, the ear drum 14 is punctured by the distal end 20. The collapsed bulb 40 is then allowed to recover enough to draw a specimen of the middle ear fluid 18 through the first hole 26 and into the hollow needle 12. The needle 12 is then withdrawn from the patient's ear. If a separate specimen container 42 is used, the distal end 20 of the needle 12 is inserted into the container 42 through its opening 44, and the now recovered bulb 40 is collapsed again to force the specimen of fluid 18 into the container 42. If the bulb 40 is used as the specimen container, the bulb 40 is adapted to draw a specimen of the middle ear fluid 18 into its chamber 32. To provide the necessary suction force, for example, the wall 30 of the bulb 40 can be made from a material that is sufficiently strong and resilient. Once the specimen has been deposited, the opening 34 to chamber 32 is then closed, for example, as described above. The specimen is now ready for subsequent culturing and identification of the bacteria present in the fluid 18.

When a self contained vacuum bulb 56 is used, the cap 62 is snapped or otherwise secured in place over the opening 34 of the test tube 58 and the membrane 60 punctured by the pointed proximal end 22, after the distal end 20 has been forced through the ear drum 14. It is desirable for the chamber 32 of the self contained vacuum bulb 56 to be sufficiently evacuated to draw a specimen of the middle ear fluid 18 through the hollow needle 12 and into the test tube 58. The test tube 58 is then withdrawn from the tubular section 63 of the cap 62. If desired, the membrane 60 can be covered by a separate sterile cap (not shown) to thereby protect the specimen from being lost or contaminated before being cultured and identified.

It may be desirable for a medicine to be disposed in the bore 24 of the hollow needle 12. This medicine can be in fluid form and disposed at the distal end 20 of the needle 12. The medicine used can be an agent used to provide topical anesthesia for deadening localized pain at the puncture site of the ear drum 14. When the collapsible bulb 40 is used, such a medicine can be applied by collapsing the bulb 40 before and/or during the insertion of the hollow needle 12 through the ear drum 14. The medicine used can also be an antibiotic for treating any infection present. With the collapsible type of bulb 40, the antibiotic is administered after the needle 12 has punctured through the ear drum 14 by collapsing the bulb 40 to expel the antibiotic into the patient's middle ear space.

From the above disclosure of the general principles of the present invention and the preceding detailed description, those skilled in this art will readily comprehend the various modifications to which the present invention is susceptible. Therefore, the scope of the invention should be limited only by the following claims and equivalents thereof.

What is claimed is:

1. An apparatus for aspirating and collecting a middle ear fluid specimen through the ear drum of a patient, said apparatus comprising:

a hollow needle having a distal end adapted for puncturing through the ear drum of a patient, a proximal end and a bore connecting a first hole at said distal end with a second hole at said proximal end; and a bulb having a wall defining at least part of a chamber and a first opening leading into said chamber, said proximal end of said hollow needle being mountable to said bulb so as to bring said second hole in fluid communication with said chamber through said first opening, wherein said needle is of sufficient length and configuration to be disposed through a speculum and puncture the ear drum, while allowing the ear drum to be viewed through the speculum, and said bulb is operatively adapted to draw a specimen of middle ear fluid through said first hole and into said hollow needle.

2. The apparatus as set forth in claim 1, wherein the wall of said bulb is collapsible and resilient enough to sufficiently recover, from a collapsed condition, to draw a specimen of middle ear fluid through said first hole and into said hollow needle.

3. The apparatus as set forth in claim 1, wherein said bulb is a self contained vacuum bulb having an evacuated chamber capable of being placed in fluid communication with said bore through said second hole and having a sufficient vacuum to draw a specimen of middle ear fluid through said first hole and into said hollow needle.

4. The apparatus as set forth in claim 1, wherein said bulb is operatively adapted to draw a specimen of middle ear fluid through said hollow needle and into said bulb, and said first opening is adapted to be closed after said hollow needle is removed therefrom.

5. The apparatus as set forth in claim 1, further comprising a stop guard secured to the outside of said hollow needle a desired distance from said first hole, said stop guard being adapted to inhibit further penetration of said hollow needle through an ear drum.

6. The apparatus as set forth in claim 1, wherein said apparatus is further suitable for preserving a middle ear specimen and further comprises a specimen container having an opening adapted for allowing the distal end of said hollow needle therethrough and containing a preservative for preserving a middle ear specimen collected by said apparatus.

7. The apparatus as set forth in claim 1, wherein said hollow needle has a tubular wall, said tubular wall has at least one perforation formed therethrough and in fluid communication with said first hole, and said apparatus includes a fluid absorbent material disposed on the outside of said hollow needle and adjacent to said at least one perforation.

8. The apparatus as set forth in claim 7, further comprising a stop guard secured to said hollow needle a desired distance from said first hole, said stop guard being adapted to inhibit further penetration of said hollow needle through an ear drum, and said at least one perforation is disposed between said stop guard and one of said first hole and said second hole.

9. The apparatus as set forth in claim 1, wherein said hollow needle includes a flared portion at said distal end, said apparatus includes a fluid absorbent material disposed on the outside of said hollow needle and adjacent to said flared portion, and said flared portion is adapted to protect said fluid absorbent material from having portions of said absorbing material dislodged while said distal end is forced through and removed from an ear drum.

10. The apparatus as set forth in claim 1, wherein a medicine is contained in said bore.

11. The apparatus as set forth in claim 1, wherein said needle is configured with a bend which allows the ear drum to be viewed through the speculum as the ear drum is punctured.

12. A method for aspirating and collecting a middle ear fluid specimen through the ear drum of a patient, said method comprising the steps of:

providing a hollow needle that is of sufficient length and configuration to be disposed through a speculum and puncture the ear drum of a patient, while allowing the ear drum to be viewed through the speculum, and a bulb that can mount the hollow needle and is operatively adapted to draw a specimen of middle ear fluid into the hollow needle when the needle is mounted on the bulb;

inserting the hollow needle through the ear drum of a patient;

causing the bulb to draw a specimen of middle ear fluid into the hollow needle; and withdrawing the hollow needle from the ear of the patient.

13. The method as set forth in claim 12, further comprising the step of:

causing the bulb to at least partially collapse, after said step of withdrawing the hollow needle, to thereby force the specimen of middle ear fluid out of the hollow needle; and directing the specimen into a specimen collection container with a preservative contained therein.

14. The method as set forth in claim 12, wherein the bulb being provided is a self contained vacuum bulb having an evacuated chamber therein and said step of causing the bulb to draw a specimen includes communicating the evacuated chamber with the bore of the hollow needle so as to draw a specimen of middle ear fluid into the hollow needle.

15. The method as set forth in claim 12, wherein the bulb being provided contains a preservative and said method further comprises the step of bringing the specimen of middle ear fluid in contact with the preservative inside of the bulb.

16. The method as set forth in claim 12, wherein the hollow needle being provided has a stop guard secured thereto, and the stop guard is adapted to inhibit full penetration of the hollow needle through the ear drum during said step of inserting the hollow needle.

17. The method as set forth in claim 12, wherein the hollow needle being provided has a tubular wall with at least one perforation formed therethrough and a fluid absorbent material disposed on the outside of the hollow needle so as to absorb fluid present in the at least one perforation, and said step of causing the bulb to draw a specimen into the hollow needle includes drawing the specimen through the hollow needle to the at least one perforation so that at least a portion of the specimen is absorbed into the absorbent material.

18. The method as set forth in claim 12, wherein the bulb being provided is collapsible and recoverable from a collapsed state, when the hollow needle is mounted thereon, so as to force air out and suction air in through the hollow needle, respectively, and said step of causing the bulb to draw a specimen includes collapsing the bulb before or after said step of inserting the hollow needle and allowing the collapsed bulb to recover enough to draw a specimen of middle ear fluid into the hollow needle.

19. The method as set forth in claim 12, wherein the bulb being provided is collapsible and recoverable from a collapsed state, when the hollow needle is mounted thereon, so as to force air out and suction air in through the hollow needle, the hollow needle is provided with a medicine disposed in its bore and said method includes collapsing the bulb to expel the medicine from the hollow needle.

20. The method as set forth in claim 12, wherein the hollow needle being provided is operatively adapted to be disposed through a speculum and to allow the ear drum to be viewed through the speculum during said step of inserting the hollow needle through the ear drum of a patient.

* * * * *